United States Patent [19]

Arai et al.

[11] Patent Number: 4,629,775
[45] Date of Patent: Dec. 16, 1986

[54] ROOM TEMPERATURE-CURABLE ORGANOPOLYSILOXANE COMPOSITION

[75] Inventors: Masatoshi Arai; Takeo Inoue; Koji Yokoo, all of Gunma, Japan

[73] Assignee: Shin-Etsu Chemical Co., Ltd., Tokyo, Japan

[21] Appl. No.: 758,164

[22] Filed: Jul. 23, 1985

[30] Foreign Application Priority Data

Jul. 24, 1984 [JP] Japan .................... 59-153554

[51] Int. Cl.$^4$ .................................. C08G 77/06
[52] U.S. Cl. ............................ 528/17; 528/18; 528/30; 528/33; 528/34
[58] Field of Search ............. 528/17, 18, 30, 33, 528/34

[56] References Cited

U.S. PATENT DOCUMENTS

| | | | |
|---|---|---|---|
| 3,647,846 | 3/1972 | Hartlein et al. | 528/17 |
| 4,036,813 | 7/1977 | Hardman et al. | 528/17 |
| 4,461,867 | 7/1984 | Suprenant | 528/17 |

Primary Examiner—Melvyn I. Marquis
Attorney, Agent, or Firm—Toren, McGeady, Stanger, Goldberg & Kiel

[57] ABSTRACT

The room temperature-curable organopolysiloxane composition of the invention can be cured into a rubbery elastomer which exhibits strong adhesion to the surface of a substrate made of, for example, a plastic resin even without the use of a primer or other adhesion aid. The composition comprises, in addition to the conventional ingredients of a silanolic hydroxy-terminated diorganopolysiloxane and alkoxy-containing organosilicon compound, a special organosilicon compound having, in a molecule, at least one group of the formula

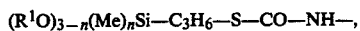

$(R^1O)_{3-n}(Me)_n Si—C_3H_6—S—CO—NH—$, in which Me is a methyl group, $R^1$ is a methyl or an ethyl group and n is zero or 1, and a titanium chelate compound represented by the general formula

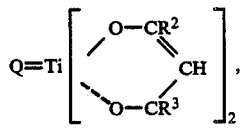

in which Q is a divalent organosilicon-containing group, $R^2$ is an alkyl group having 1 to 3 carbon atoms and $R^3$ is the same as $R^2$ or $R^2O$.

4 Claims, No Drawings

ROOM TEMPERATURE-CURABLE ORGANOPOLYSILOXANE COMPOSITION

BACKGROUND OF THE INVENTION

The present invention relates to a room temperature-curable organopolysiloxane composition which can be cured by the mechanism of dealcoholation condensation reaction to give a cured rubbery elastomer having good adhesion to the surface of a substrate such as plastics.

As a recent trend, devices and instruments in electric and electronic industries are desired to be designed in more and more compact forms for several reasons. In addition, it is also a recent trend that the housings of such devices and instruments are shaped of a plastic resin such as polycarbonate, polybutylene terephthalate, acrylic, nylon, ABS, polyvinyl chloride and the like thermoplastic resins. The industries of building construction and vehicles for trnsportation are also along this trend of increasing use of plastics in many parts and the plastics used in these fields include acrylic resins, polycarbonate resins, polyvinyl chloride resins and the like.

It is usual that the plastic-made parts are jointed together by use of a silicone sealant or a room temperature-curable organopolysiloxane composition for adhesive bonding and sealing while good adhesion of a silicone sealant to the surface of a plastic-made part is obtained only by the indispensable use of a primer. Since most of the primers for such a use are supplied in the form of a solution in an organic solvent, a very serious problem is caused by the use of a primer on to the surface of a plastic-made part which absorbs the organic solvent to be eventually cracked in the adhesively bonded or sealed part. Therefore, it has been eagerly desired to develop a room temperature-curable organopolysiloxane composition which can exhibit good adhesion on to the surface of a plastic-made body without using a primer when it is cured in contact with the substrate surface.

SUMMARY OF THE INVENTION

It is therefore an object of the present invention to provide a room temperature-curable organopolysiloxane composition, which is referred to as RTV composition hereinbelow, free from the above described problems in the prior art RTV compositions and capable of exhibiting good adhesion on to the surface of a plastic-made substrate even by use of no primer.

Thus, the room temperature-curable organopolysiloxane composition of the invention comprises:

(a) 100 parts by weight of a diorganopolysiloxane having a viscosity in the range from 100 to 1,000,000 centistokes at 25° C. and terminated at both molecular chain ends each with a silanolic hydroxy group;

(b) from 1 to 20 parts by weight of an alkoxysilane or an alkoxy-containing organopolysiloxane having at least three alkoxy groups directly bonded to the silicon atom or atoms in a molecule, the other organic group or groups bonded to the silicon atom or atoms being each a monovalent hydrocarbon group;

(c) from 0.05 to 10 parts by weight of an organosilicon compound having, in a molecule, at least one organosilicon-containing group represented by the general formula $$(R^1O)_{3-n}(Me)_nSi-C_3H_6-S-CO-NH-, \quad (I)$$

in which Me is a methyl group, $R^1$ is a methyl or an ethyl group and n is zero or 1; and (d) from 0.1 to 10 parts by weight of a titanium chelate compound represented by the general formula

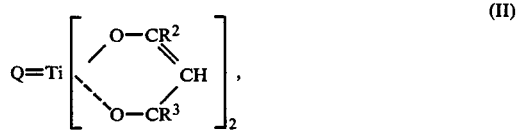

in which Q is a divalent organosilicon-containing group, $R^2$ is an alkyl group having 1 to 3 carbon atoms and $R^3$ is the same as $R^2$ or $R^2O$.

DETAILED DESCRIPTION OF THE PREFERRED EMBODIMENTS

The diorganopolysiloxane as the component (a) in the inventive RTV composition is a base ingredient conventionally used as the principal ingredient of RTV compositions. The diorganopolysiloxane is composed of a repetition of the diorganosiloxane units of the formula $-SiR_2-O-$ and both of the molecular chain terminals are blocked each with a silanolic hydroxy group, i.e. a hydroxy group directly bonded to the silicon atom. The organic group R in the above given unit formula should be a monovalent hydrocarbon group selected from the class consisting of alkyl groups, e.g. methyl, ethyl, propyl and butyl groups, cycloalkyl groups, e.g. cyclopentyl and cyclohexyl groups, alkenyl groups, e.g. vinyl and allyl groups, aryl groups, e.g. phenyl, tolyl and naphthyl groups, and aralkyl groups, e.g. benzyl and 2-phenylethyl groups, as well as those substituted groups obtained by the replacement of a part or all of the hydrogen atoms in the above named hydrocarbon groups with substituent atoms or groups such as halogen atoms, cyano groups and amino groups.

The diorganopolysiloxane as the component (a) should have such a degree of polymerization that the viscosity thereof is in the range from 100 to 1,000,000 centistokes or, preferably, from 1,000 to 50,000 centistokes at 25° C. The reasons for this viscosity limitation are that a RTV composition formulated with a diorganopolysiloxane having a too low viscosity cannot give a cured elastomer having a sufficiently high mechanical strength while a RTV composition formulated with a diorganopolysiloxane of an excessively high viscosity has an extremely high consistency so that the workability or working efficiency therewith is unavoidably decreased.

The component (b), which is an alkoxy-containing organosilane or organopolysiloxane compound, having at least three alkoxy groups directly bonded to the silicon atom or atoms in a molecule, is also conventional as a crosslinking agent in RTV compositions. The alkoxy groups are exemplified by methoxy, ethoxy, n-propoxy and isopropoxy groups as well as alkoxy-substituted alkoxy groups such as those of the formulas $MeO-CH_2O-$, $MeO-CH_2CH_2O-$, $EtO-CH_2O-$ and $EtO-CH_2CH_2O-$, in which Me and Et denote a methyl and an ethyl group, respectively. The organic groups, if any, of the compound other than the alkoxy groups should be each a monovalent hydrocarbon group exemplified by those given before as the examples of the groups R in the component (a).

The amount of the component (b) in the inventive RTV composition should be in the range from 1 to 20 parts by weight or, preferably, from 2 to 10 parts by weight per 100 parts by weight of the component (a). When the amount of the component (b) is too small, the resultant composition is poor in the curability not to give a fully cured elastomer while the cured body obtained by curing a RTV composition formulated with an excessively large amount of the component (b) would be hard and brittle without the desired rubbery elasticity and physical properties.

The component (c) is the characteristic ingredient in the inventive RTV composition which serves to impart the adhesiveness of the cured composition to the substrate surface on which the RTV composition has been cured. The compound of this component essentially contains at least one organosilicon-containing group of the general formula (I) given above, in which each of the symbols has the meaning defined above. Several of the examples of the compound suitable as the component (c) include those expressed by the following formulas: $A^1$—Ph; $A^1$—$(C_6H_4)$—$CH_2$—$(C_6H_4)$—$A^1$; $A^2$—$(C_6H_4)$-$(CH_2$—$C_6H_3A^2)_n$$CH_2$—$(C_6H_4)$—$A^2$; $A^3$—$C_6H_3Me$—$A^3$ in which $C_6H_3Me$ is a 2,4- or 2,6-tolylene group; a cyclic compound of the formula (—CO—$NA^1$—)$_3$; EtC(—$CH_2O$—CO—NH—$C_6H_3Me$—$A^1$)$_3$; and EtC[—$CH_2O$—CO—NH-$(CH_2)_6$$A^1$]$_3$ in which Me, Et, Ph and ($C_6H_4$) denote metyl, ethyl, phenyl and phenylene groups, respectively, and $A^1$, $A^2$ and $A^3$ each denote the specific organosilicon-containing groups of the following formulas.

$A^1$: $(MeO)_3Si$—$C_3H_6$—S—CO—NH—
$A^2$: $(MeO)_2SiMe$—$C_3H_6$—S—CO—NH—
$A^3$: $(EtO)_3Si$—$C_3H_6$—S—CO—NH—.

These organosilicon compounds can be prepared by the reaction of a 3-mercaptopropyl-containing alkoxysilane and various kinds of isocyanato compounds of the formula OCN—R', R' being a monovalent organic group, in the presence of a catalyst according to the following reaction equation:

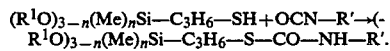

$(R^1O)_{3-n}(Me)_nSi$—$C_3H_6$—SH+OCN—R'→(-$R^1O)_{3-n}(Me)_nSi$—$C_3H_6$—S—CO—NH—R'.

The catalyst is preferably a metal carboxylate such as lead 2-ethylhexoate, dibutyltin diacetate, cobalt naphthenate, zinc stearate and the like and the reaction may be performed, if necessary, in an organic solvent such as benzene, toluene, xylene and the like.

The amount of the component (c) in the inventive RTV composition should be in the range from 0.05 to 10 parts by weight or, preferably, from 0.5 to 3 parts by weight per 100 parts by weight of the component (a). This is because no desired improvement in the adhesive bonding can be obtained by a too small amount of the component (c) as a matter of course while a RTV composition formulated with an excessively large amount of the composition gives a cured body having a too high hardness as a rubbery elastomer.

The component (d) serves as a catalyst which effects stabilization of the inventive RTV composition and is a chelate compound of titanium represented by the general formula (II) given before, in which Q is a divalent organosilicon-containing group described below, $R^2$ is an alkyl group having 1 to 3 carbon atoms, i.e. methyl, ethyl or propyl group, and $R^3$ is an alkyl group having 1 to 3 carbon atoms as mentioned above or an alkoxy group having 1 to 3 carbon atoms such as methoxy, ethoxy and propoxy groups. Examples of the divalent organosilicon-containing group denoted by Q are as follows, denoting methyl, propyl and phenyl groups with Me, Pr and Ph, respectively:

$Q^1$: —O—$SiMe_2$—O—$SiMe_2$—O—;
$Q^2$: —O—SiMePh—O—;
$Q^3$: —O—$SiPh_2$—O—;
$Q^4$: —O-$(SiMe_2$—O$)_4$; and $Q^5$: 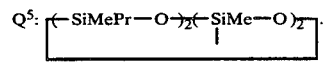

Accordingly, several of the examples of the titanium chelate compound as the component (d) include those compounds of the formula (II) in which:

Q is $Q^1$, $R^2$ is methyl and $R^3$ is ethoxy;
Q is $Q^2$, $R^2$ is methyl and $R^3$ is methoxy;
Q is $Q^3$, $R^2$ is methyl and $R^3$ is methyl;
Q is $Q^4$, $R^2$ is methyl and $R^3$ is ethoxy; and
Q is $Q^5$, $R^2$ is methyl and $R^3$ is ethyl.

These titanium chelate compounds can be prepared by the reaction of an orthotitanate ester with a β-diketone or a β-ketoester followed by the reaction with a disilanolic organosilicon compound of the formula H—Q—H, in which Q has the same meaning as defined above. The reaction is performed usually at 40° to 70° C. It is optional to perform the reaction in an organic solvent such as toluene although the reaction can proceed in most cases without use of a solvent. When the orthotitanate ester is reacted with a β-ketoester, an alcohol is produced as a byproduct which, however, should not necessarily be removed before the reaction with the disilanolic organosilicon compound.

The amount of th component (d) in the inventive RTV composition should be in the range from 0.1 to 10 parts by weight or, preferably, from 0.5 to 3 parts by weight per 100 parts by weight of the component (a). This is because no stabilizing effect of the composition can be obtained with a too small amount of the component (d) as a matter of course while a too large amount of the component may unduly retard the curing reaction of the composition.

The inventive RTV composition can be prepared by uniformly blending the above described components (a) to (d) in a suitable blending machine which is not limitative to a machine of specific types. It is optional that the RTV composition is admixed with a reinforcing or non-reinforcing filler such as a fumed silica filler which may be surface-treated, if desired, with hexametñyldisilazane, oligomeric cyclic dimethylpolysiloxane and the like, precipitated silica, quartz powder, diatomaceous earth, titanium dioxide, aluminum oxide, lead oxide, iron oxide, carbon black, bentonite, graphite powder, calcium carbonate, mica flakes, clay, glass beads, glass microballoons, glass fibers, beads of a synthetic resin, e.g. polyvinyl chloride, polystyrene and acrylic resin, and others.

It is further optional that the inventive RTV composition is admixed with various kinds of known additives conventionally used in RTV compositions including plasticizers, coloring agents, e.g. pigments, flame retardant agents, thixotropy improvers, bactericidal and fungicidal agents, adhesion improvers such as the so-called carbon-functional silanes having amino, epoxy, mercapto and other functional groups although the amounts of these additives should be limited not to unduly affect the properties of the inventive RTV composition.

In the following, RTV compositions according to the invention are described in more detail by way of examples as preceded by the description of the preparation of the titanium chelate compounds used as the component (d) and the organosilicon compounds as the component (c). In the following description, the expression of "parts" always refers to "parts by weight" and the values of viscosity are those obtained by the measurements at 25° C.

Preparation 1

Into 284.3 g of tetra(isopropyl) titanate under agitation contained in a 1-liter capacity flask equipped with a stirrer, thermometer and reflux condenser were added dropwise 260.2 g of ethyl acetoacetate in a stream of nitrogen gas over a period of about 1 hour. The temperature of the reaction mixture was gradually increased during this period up to 56° C. After completion of the dropwise addition of the acetoacetate, the reaction mixture was further heated under agitation at 60° C. for additional 2 hours and then 14.7 g of 1,7-dihydroxy octamethyl tetrasiloxane were added to the mixture taking 30 minutes followed by heating of the mixture at 60° C. for 2 hours to complete the reaction. The reaction mixture after completion of the reaction was subjected to stripping under reduced pressure to remove low-boiling fractions and to give 611 g of a yellowish brown liquid product having a viscosity of 230 centistokes, which could be identified by the infrared absorption spectroscopy and NMR analysis to be the titanium chelate compound of the formula (II) in which Q is $Q^4$, $R^2$ is methyl and $R^3$ is ethoxy. This compound is referred to as titanium chelate I hereinbelow.

Preparations 2 to 4

Titanium chelate compounds each in the form of a yellowish brown, clear liquid, referred to as titanium chelates II, III and IV hereinbelow, were prepared each in substantially the same procedure as in Preparation 1 above excepting the replacement of the 1,7-dihydroxy octamethyl tetrasiloxane with another disilanolic organosilicon compound as indicated below to give the indicated amount of the product.

Titanium chelate II: 216.3 g of diphenylsilane diol, yield of the product: 502 g.
Titanium chelate III: 356.6 g of 1,3,5-trimethyl-1,3-dipropyl-7-hydroxy cyclotrisiloxane, yield of the product: 643 g.
Titanium chelate IV: 166.3 g of 1,1,3,3-tetramethyl-1,3-dihydroxy disiloxane, yield of the product: 452 g.

These titanium chelate compounds were identified each to be the compound of the formula (II) in which Q was $Q^3$, $R^2$ was methyl and $R^3$ was ethoxy for the titanium chelate II, Q was $Q^5$, $R^2$ was methyl and $R^3$ was ethoxy for the titanium chelate III, and Q was $Q^1$, $R^2$ was methyl and $R^3$ was ethoxy for the titanium chelate IV, respectively.

Preparation 5

Into a 100 ml capacity flask equipped with a stirrer, thermometer and reflux condenser were introduced 25 g of toluene and 0.1 g of dibutyltin dilaurate to form a mixture, into which a mixture composed of 17.4 g of tolylene diisocyanate and 39.3 g of 3-mercaptopropyl trimethoxysilane was added dropwise under agitation over a period of about 2 hours. The temperature of the reaction mixture was gradually increased during this period up to 70° C. After completion of the dropwise addition of the mixture, the reaction mixture was further agitated at 70° C. for additional 4 hours to complete the reaction. Thereafter, the reaction mixture was stripped to remove the solvent under reduced pressure to give 54.3 g of a viscous, clear, colorless liquid product, which could be identified by analyses to be the organosilicon compound of the formula $A^1$—$C_6H_3Me$—$A^1$. This product is referred to merely as compound I hereinbelow.

Preparations 6 to 9

Organosilicon compounds as the component (c), referred to as compounds II, III, IV and V hereinbelow, were prepared each in substantially the same manner as in Preparation 5 described above excepting the replacement of the tolylene diisocyanate with another isocyanato compound in an amount indicated below. The yield and appearance of each of the product compounds are also given.

Compound II: 25.0 g of cyclohexyl isocyanate, yield of the colorless, clear liquid product 62.5 g.
Compound III: 23.8 g of phenyl isocyanate, yield of the colorless, clear liquid product 60.6 g.
Compound IV: 25.0 g of bis(4-isocyanatophenyl)methane, yield of the yellowish brown, a clear liquid product: 61.6 g.
Compound V: 33.7 g of a cyclic compound of the formula $$\begin{array}{c} +\text{CO}-\text{N}\!\!\!\!\!\!+_{\overline{3}}, \\ | \\ -\text{C}_3\text{H}_6-\text{NCO} \end{array}$$

yield of the clear, colorless liquid product: 70.3 g.

These compounds could be identified each to be the compound of the formula $C_6H_{11}$—$A^1$ (compound II), $C_6H_5$—$A^1$ (compound III), $CH_2(-C_6H_4-A^1)_2$ (compound IV) or cyclic formula of $$\begin{array}{c} +\text{CO}-\text{N}\!\!\!\!\!\!+_{\overline{3}}\text{(compound V)}, \\ | \\ -\text{C}_3\text{H}_6-A^1 \end{array}$$

respectively.

Preparation 10

The synthetic procedure was substantially the same as in Preparation 5 described above except that 3-mercaptopropyl trimethoxysilane was replaced with 36.1 g of 3-mercaptopropyl methyl dimethoxysilane to give 51.5 g of a clear, colorless liquid product which could be identified to be a compound of the formula $A^2$—$C_6H_3Me$—$A^2$. This product is referred to as the compound VI hereinbelow.

EXAMPLE 1

A base compound was prepared by uniformly blending equal amounts by weight of a dimethylpolysiloxane having a viscosity of 20,000 centistokes and terminated at both molecular chain ends each with a silanolic hydroxy group and a calcium carbonate filler.

RTV compositions No. 1 to No. 9 were prepared each by uniformly blending under an anhydrous condition 100 parts of the above prepared base compound, either one of the titanium chelates I, II, III and IV prepared in Preparations and either one of the compounds I, II, III, IV, V and VI prepared in the Preparations in amounts indicated in Table 1 below together with an alkoxysilane which was methyl trimethoxysilane (alkoxysilane I), methyl triethoxysilane (alkoxysilane II) or methyl tris(methoxy-substituted methoxy)silane (alkoxysilane III) in an amount also indicated in Table 1.

For comparison, RTV composition No. 10 was prepared in a similar manner with omission of the compounds I to VI and replacement of the titanium chelate compound with a similar titanium chelate of the formula (II) in which $R^2$ was methyl and $R^3$ was ethoxy but the group denoted by Q was replaced with two isopropyl groups instead of a divalent organosilicon group.

TABLE 1

| Composition No. | Alkoxysilane (parts) | Titanium chelate (parts) | Compound (parts) |
|---|---|---|---|
| 1 | I (3.0) | I (1.0) | I (0.1) |
| 2 | I (3.0) | I (1.0) | I (1.0) |
| 3 | I (3.0) | I (3.0) | I (5.0) |
| 4 | I (5.0) | II (1.0) | III (1.0) |
| 5 | II (5.0) | II (3.0) | II (1.0) |
| 6 | II (5.0) | III (2.0) | IV (5.0) |
| 7 | III (3.0) | IV (1.0) | IV (1.0) |
| 8 | III (3.0) | I (1.0) | V (1.0) |
| 9 | I (7.0) | I (3.0) | VI (1.0) |
| 10 | I (3.0) | (*) (1.0) | — |

(*) See text.

These RTV compositions were subjected to the test of the adhesive bonding strength using a pair of test panels of an acrylic resin or a polycarbonate resin each having dimensions of 50 mm by 50 mm by 5 mm to prepare test specimens according to JIS A 5758. These test specimens were kept in an atmosphere of 55% relative humidity first at 20° C. for 14 days and then at 30° C. for 14 days to cure the RTV composition. The test specimens with the RTV composition as cured were further dipped in water at 50° C. for 7 days. The test for the adhesive bonding undertaken with the test specimens as cured and after dipping in water gave the results of the 50% modulus, tensile strength, ultimate elongation and percentage of cohesive failure shown in Tables 2 and 3 for the acrylic resin test panels and for the polycarbonate resin test panels, respectively. In each of the tables, the data in brackets are the values obtained by the measurements after dipping in water.

TABLE 2

| Composition No. | 50% modulus, kg/cm² | Tensile strength, kg/cm² | Ultimate elongation, % | Cohesive failure, % |
|---|---|---|---|---|
| 1 | 3.0 (2.8) | 8.5 (8.2) | 310 (320) | 70 (50) |
| 2 | 2.8 (2.6) | 8.5 (8.2) | 280 (290) | 100 (100) |
| 3 | 2.5 (2.5) | 7.7 (7.6) | 400 (400) | 100 (100) |
| 4 | 3.0 (3.0) | 9.3 (9.0) | 350 (370) | 100 (100) |
| 5 | 3.0 (2.8) | 9.2 (9.0) | 330 (350) | 20 (30) |
| 6 | 2.5 (2.4) | 7.2 (7.1) | 430 (440) | 100 (100) |
| 7 | 3.3 (3.2) | 10.5 (10.2) | 360 (350) | 100 (100) |
| 8 | 3.0 (2.9) | 9.2 (8.5) | 320 (340) | 100 (100) |
| 9 | 2.8 (2.9) | 7.8 (7.8) | 310 (330) | 100 (100) |
| 10 | 3.3 (2.9) | 4.5 (3.5) | 80 (60) | 0 (0) |

TABLE 3

| Composition No. | 50% modulus, kg/cm² | Tensile strength, kg/cm² | Ultimate elongation, % | Cohesive failure, % |
|---|---|---|---|---|
| 1 | 3.1 (3.0) | 8.9 (8.2) | 340 (360) | 100 (100) |
| 2 | 2.7 (2.6) | 9.5 (9.4) | 380 (390) | 100 (100) |
| 3 | 2.6 (2.6) | 9.3 (9.0) | 360 (380) | 100 (100) |
| 4 | 3.2 (3.2) | 10.0 (9.5) | 400 (400) | 100 (100) |
| 5 | 3.1 (3.0) | 10.2 (9.2) | 420 (390) | 50 (40) |
| 6 | 2.7 (2.5) | 9.8 (9.0) | 390 (350) | 100 (100) |
| 7 | 3.1 (3.0) | 9.5 (9.0) | 360 (350) | 100 (100) |
| 8 | 3.2 (3.0) | 10.3 (9.3) | 430 (400) | 100 (100) |
| 9 | 2.9 (2.8) | 8.8 (8.4) | 340 (310) | 100 (100) |
| 10 | 3.2 (—) | 4.3 (4.0) | 60 (30) | 0 (0) |

EXAMPLE 2

The RTV compositions No. 2 and No. 10 prepared in the preceding example were spread by rolling each into a sheet of 2 mm thickness which was cured by standing in an atmosphere of 55% relative humidity at 20° C. for 7 days. For comparison, the RTV compositions were heated for 5 days in a drying oven at 70° C. and then spread each into a sheet of 2 mm thickness which was kept standing for 7 days under the same curing conditions as above. The thus obtained rubbery sheets of the RTV compositions either with or without the thermal aging at 70° C. were subjected to the measurement of the mechanical properties according to the procedure specified in JIS K 6301 to give the results shown in Table 4 below.

TABLE 4

| Composition No. | Thermal aging at 70° C. | Hardness, JIS scale | Tensile strength, kg/cm² | Ultimate elongation, % |
|---|---|---|---|---|
| 2 | No | 25 | 20 | 650 |
|  | Yes | 22 | 19 | 640 |
| 10 | No | 27 | 21 | 630 |
|  | Yes |  | No curing |  |

What is claimed is:

1. A room temperature-curable organopolysiloxane composition which comprises:
   (a) 100 parts by weight of a diorganopolysiloxane having a viscosity in the range from 100 to 1,000,000 centistokes at 25° C. and terminated at both molecular chain ends each with a silanolic hydroxy group;
   (b) from 1 to 20 parts by weight of an alkoxysilane or an alkoxy-containing organopolysiloxane having at least three alkoxy groups directly bonded to the silicon atom or atoms in a molecule, the other organic group or groups bonded to the silicon atom or atoms being each a monovalent hydrocarbon group;
   (c) from 0.05 to 10 parts by weight of an organosilicon compound having, in a molecule, at least one organosilicon-containing group represented by the general formula

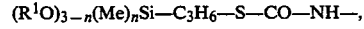
   $(R^1O)_{3-n}(Me)_n Si-C_3H_6-S-CO-NH-$, in which Me is a methyl group, $R^1$ is a methyl or an ethyl group and n is zero or 1; and
   (d) from 0.1 to 10 parts by weight of a titanium chelate compound represented by the general formula

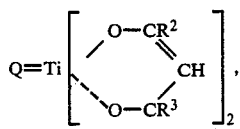

in which Q is a divalent organosilicon-containing group, $R^2$ is an alkyl group having 1 to 3 carbon atoms and $R^3$ is the same as $R^2$ or $R^2O$.

2. The room temperature-curable organopolysiloxane composition as claimed in claim 1 wherein the diorganopolysiloxane as the component (a) has a viscosity in the rang from 100 to 1,000,000 centistokes at 25° C.

3. The room temperature-curable organopolysiloxane composition as claimed in claim 1 wherein the divalent organosilicon-containing group denoted by Q in the component (d) is selected from the class consisting of the groups expressed by the formulas: $-O-SiMe_2-O-SiMe_2-O-$; $-O-SiMePh-O-$; $-O-SiPh_2-O-$; $-O(-SiMe_2-O-)_4$; and

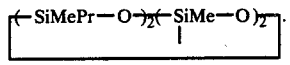

4. The room temperature-curable organopolysiloxane composition as claimed in claim 1 wherein the organosilicon compound as the component (c) is selected from the class consisting of the compounds expressed by the formulas: $A^1-Ph$; $A^1-(C_6H_4)-CH_2-(C_6H_4)-A^1$; $A^2-(C_6H_4)(-CH_2-C_6H_3A^2-)_n CH_2-(C_6H_4)-A^2$; $A^3-C_6H_3Me-A^3$, a cyclic formula $(-CO-NA^1-)_3$; $EtC(-CH_2O-CO-NH-C_6H_3Me-A^1)_3$; and $EtC[-CH_2O-CO-NH(-CH_2-)_6; A^1]_3$ in which Me, Et, Ph and $(C_6H_4)$ denote metyl, ethyl, phenyl and phenylene groups, respectively, $C_6H_3Me$ is a 2,4- or 2,6-tolylene group; and $A^1$, $A^2$ and $A^3$ each denote an organosilicon-containing group of the formulas: $(MeO)_3Si-C_3H_6-S-CO-NH-$; $(MeO)_2SiMe-C_3H_6-S-CO-NH-$; or $(EtO)_3Si-C_3H_6-S-CO-NH-$, respectively.

* * * * *